(12) United States Patent
Goswami et al.

(10) Patent No.: US 6,288,227 B1
(45) Date of Patent: Sep. 11, 2001

(54) SOLUBLIZED 2,6-DINAPHTHYLAMINOTRIAZINES

(75) Inventors: Ramanuj Goswami, Webster; Jean M. Buongiorne, Brockport; Mary E. Craver, Rochester, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/679,922

(22) Filed: Oct. 5, 2000

(51) Int. Cl.⁷ .............................. C07D 251/70; G03C 5/58
(52) U.S. Cl. ........................................ 544/197; 430/468
(58) Field of Search ................................................ 544/197

(56) References Cited

U.S. PATENT DOCUMENTS 3,400,121 * 9/1968 Weckler et al. ........................ 544/197

FOREIGN PATENT DOCUMENTS

WO 97/10887    3/1997  (WO) .

* cited by examiner

Primary Examiner—Mukund J. Shah
Assistant Examiner—Venkataraman Balasubramanian
(74) Attorney, Agent, or Firm—J. Lanny Tucker

(57) ABSTRACT

Compounds represented by Structure I

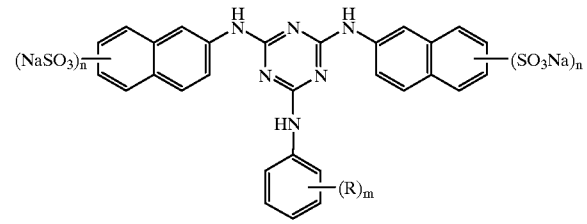

wherein R is carboxy or sulfo, m is an integer of from 0 to 7 and n is an integer of from 2 to 5 as useful in concentrated aqueous photographic processing compositions.

3 Claims, No Drawings

SOLUBLIZED 2,6-DINAPHTHYLAMINOTRIAZINES

FIELD OF THE INVENTION

This invention relates to novel water-soluble 2,6-dinaphthylaminotriazines that have utility in photographic processing compositions.

BACKGROUND OF THE INVENTION

The conventional image-forming process of silver halide photography includes imagewise exposure of a photographic silver halide recording material to actinic radiation (such as actinic light), and the eventual manifestation of a useable image by wet photochemical processing of that exposed material. A fundamental step of photochemical processing is the treatment of the material with one or more developing agents to reduce silver halide to silver metal. With black-and-white photographic materials, the metallic silver usually comprises the image. With color photographic materials, the useful image consists of one or more images in organic dyes produced from an oxidized developing agent formed wherever silver halide is reduced to metallic silver.

To obtain useful color images, it is usually necessary to remove all of the silver from the photographic element after color development. This is sometimes known as "desilvering". Removal of silver is generally accomplished by oxidizing the metallic silver, and then dissolving it and undeveloped silver halide with a "solvent" or fixing agent in what is known as a fixing step. Oxidation is achieved with an oxidizing agent, commonly known as a bleaching agent.

Fixing is typically carried out using a fixing composition that includes one or more fixing agents such as thiosulfate salts. Both ammonium and sodium thiosulfate salts are known. Fixing solutions containing ammonium ions are preferred for providing more rapid fixing, but they present environmental concerns. Thus, fixing solutions containing sodium ions, while slower, are also advantageous.

Color photographic silver halide materials often contain various sensitizing dyes that extend the inherent photosensitivity of the photosensitive silver halide emulsions to electromagnetic radiation. One important class of such sensitizing dyes are carbocyanine sensitizing dyes that are commonly included in silver halide emulsion layers in photographic silver halide films, for example in color reversal photographic silver halide films (films normally used to provide positive color images).

Many photographic silver halide elements contain residual sensitizing dyes after photoprocessing. In some cases, the level of retained sensitizing dyes is inconsequential and thus, unobservable. In other instances, however, the high level of retained sensitizing dye results in undesirably high dye stain (or unwanted color) in the elements.

The problems with residual sensitizing dyes have also been satisfactorily addressed by incorporating certain stain reducing agents into one or more working strength photographic processing compositions. These compounds are described in copending and commonly assigned U.S. Ser. No. 09/464,551 filed Dec. 16, 1999 by Goswami et al and U.S. Ser. No. 09/464,961 filed Dec. 16, 1999 by Goswami et al as colorless or slightly yellow compounds having an extended planar π system that is devoid of a diaminostilbene fragment or fused triazole nuclei. While these compounds can be incorporated into various photoprocessing compositions, it is preferred to include them in concentrated photographic fixing compositions.

However, when attempts were made to incorporate some of these stain reducing agents into concentrated processing solutions such as concentrated aqueous photographic fixing solutions, it found that several of them did not pass rigorous solubility tests. For example, many of them showed unacceptable solubility even when organic solvents were added, insolubility in solution at low temperature for lengthy times, or insolubility in concentrated fixing composition.

WO 97/10887 (Lowe et al) describes affinity ligands useful in the purification of proteins. These compounds include hundreds of possible ligands that may include 2,6-dinaphthylaminotriazines. This reference also describes some methods for making such ligands.

There remains a need for solubilized 2,6-dinaphthylaminotriazines that can be incorporated into concentrated photographic processing compositions that meet all manufacturing, customer use, and storage stability requirements.

SUMMARY OF THE INVENTION

This invention provides compounds represented by the following Structure I

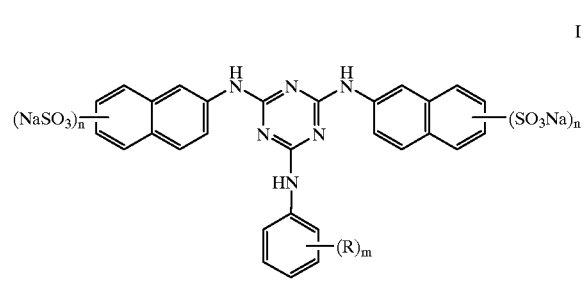

wherein R is carboxy or sulfo, m is an integer of from 0 to 5 and n is an integer of from 2 to 7.

The compounds of this invention are suitably soluble in water that they can be readily incorporated into concentrated photographic processing compositions including photographic color developing, bleaching, bleach/fixing and fixing compositions without causing undesired precipitation of various components. The compounds can also be formulated and packaged in concentrated aqueous form as "additive fixer compositions".

The compounds of Structure I also meet the following minimal stability standards that are particular to their use in photographic processing compositions:

a) they are soluble at 33 g in 500 ml of water, b) they have low temperature solubility that is determined by placing 100 ml aqueous samples of the compounds in closed containers and holding them individually it at 0° F. (−18° C.), 20° F. (−7° C.), 30° F. (−1° C.), 40° F. (4° C.), 50° F. (10° C.) and 70° F. (21° C.) for 14 days and then observing the samples 24 hours later for signs of precipitation or other observable changes (for example color, presence of haze, or phase separation), and c) they cause no precipitation at 33 g in a 18.9 liter volume of commercially available KODAK Fixer and Replenisher Process E-6 AR at room temperature for at least 3 days (preferably at least 10 days).

DETAILED DESCRIPTION OF THE INVENTION

The 2,6-dinaphthylaminotriazine compounds represented by Structure I have at least four sulfonate solubilizing groups attached to the naphthyl rings and specific substituents attached to the triazine ring.

The compounds of this invention are represented by Structure I:

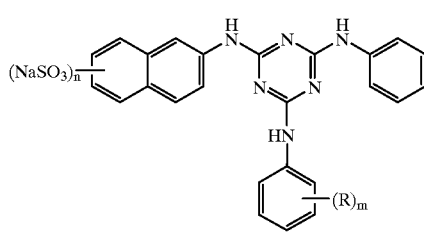

wherein R is carboxy (or salt thereof) or sulfo (or salt thereof), m is an integer of from 0 to 5, and n is an integer of from 2 to 7. Preferably, R is carboxy, m is an integer of 1 to 2, and n is 2.

Representative compounds within Structure I are the following Compounds I-1 to I-7:

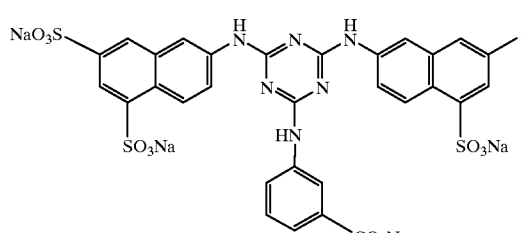

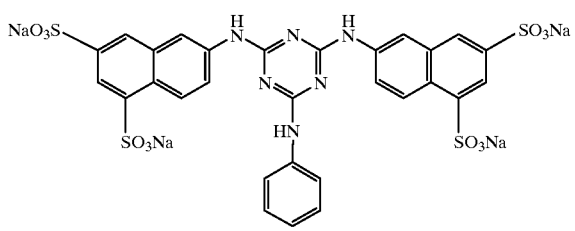

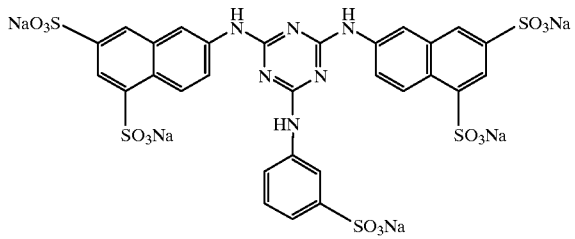

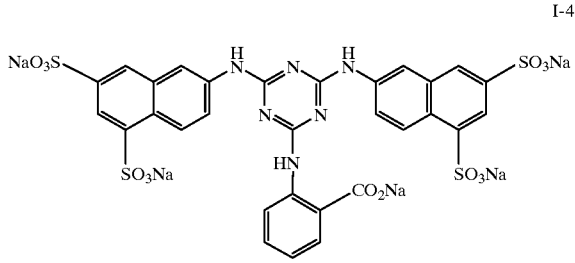

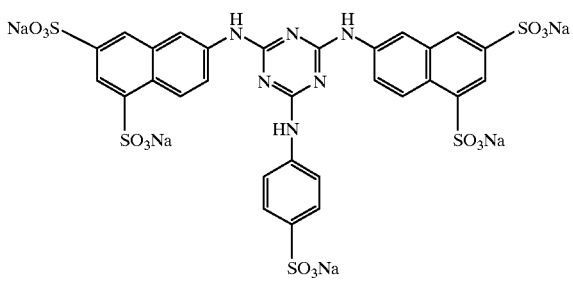

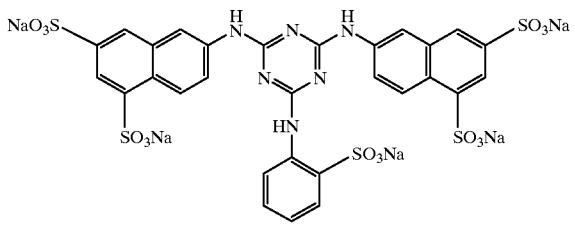

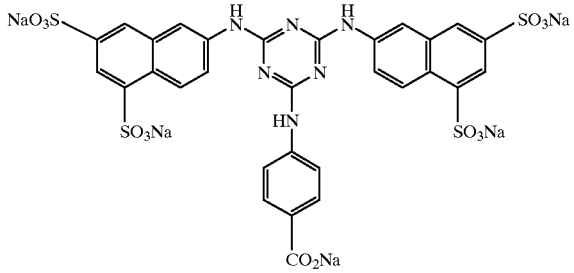

Compound I-1 (or similar potassium salt) noted above is most preferred for use in the preferred photographic fixing compositions.

These 2,6-dinaphthylaminotriazine compounds can be prepared using the methods described for example in WO 97/10887. The starting materials can be obtained from various commercial sources, including TCI-America.

In general, a preferred method includes the following reaction scheme for preparing Compound I-1 of the present invention is provided as follows:

Synthetic Scheme

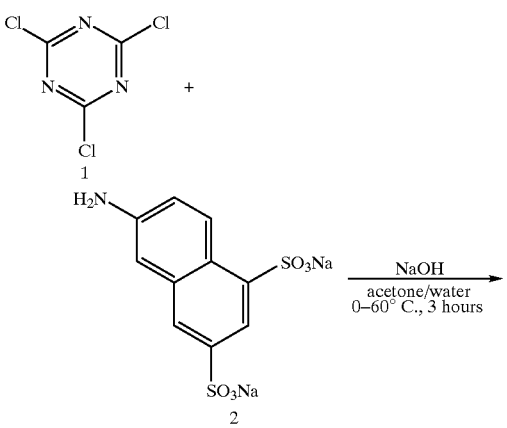

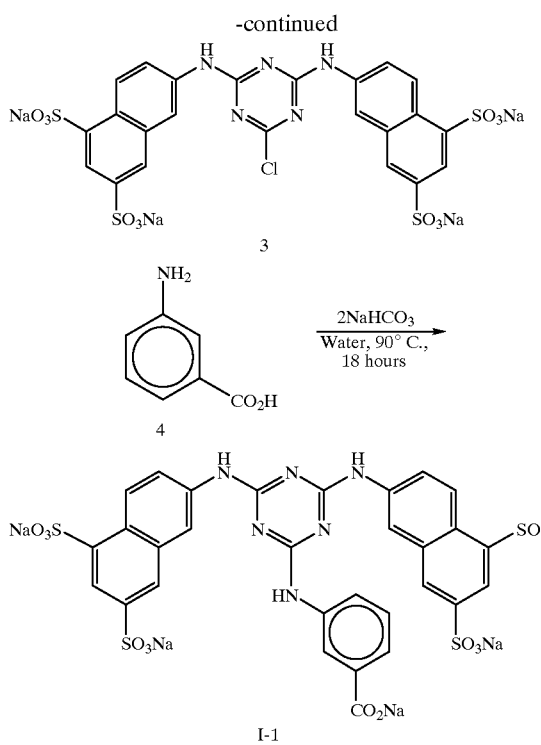

The products can be isolated by adding acetone or acetone-methanol mixtures to the reaction mixtures. The products can also be readily characterized by conventional liquid chromatographic and mass spectra analyses.

The following examples are provided to illustrate synthesis of a preferred compound of this invention and the utility of several of the compounds, and are not to be limiting in any fashion.

EXAMPLE 1
Preparation of Compound I-1

Reference is made to the Synthetic Scheme noted above in this synthetic preparation. Cyanuric chloride (1, 133.0 g, 0.72 mole) was dissolved in 3 liters of acetone in a 12-liter flask equipped with a mechanical stirrer. Crushed ice (3 kg) was added to it. To this cold mixture was added all at once, while stirring, a solution containing 6-amino-1,3-naphthalenedisulfonic acid disodium salt (2, 605 g, 88% purity, 1.53 mole) in 1800 ml water and 1200 g of ice. An aqueous solution (200 ml) of sodium hydroxide (57.6 g, 1.44 mole) was added portion-wise with stirring to the resulting mixture, as the reaction pH became acidic. The first 100 ml portion was added over 15 minutes while the reaction temperature was still less than 0° C. This reaction mixture was then heated gradually by using a steam bath. The remaining 100 ml were added gradually over the next 1.25 hours while the reaction temperature was raised to 60° C. The reaction mixture was stirred at 60° C. for an additional 2 hours and was then cooled to room temperature.

The resulting reaction mixture was slowly poured into a solvent mixture containing 60 liters of acetone and 6 liters of methanol, while stirring. It was then allowed to settle overnight and 40 liters of solvent was removed by decanting. The resulting solid was collected on an 11.5 inch (29.2 cm) diameter funnel using a VWR #413 filter paper. The solid was then washed with acetone and P950 ligroin, and was air-dried on the funnel. The resulting solid clumps were crushed and the powder was dried in a vacuum oven overnight, giving rise to 560 g (yield: 96.5%) of the desired chloro product, 3.

Sodium bicarbonate (118 g, 1.4 mole) was added to 2.5 liters of water in a 5-liter flask. 3-Aminobenzoic acid (4, 92 g, 0.67 mole) was added portion-wise to this solution while being heated to 85° C. The chloro derivative compound (3, 550 g, 0.68 mole) was added to this solution portion-wise over a period of 15 minutes. The resulting mixture was heated at 85–90° C. overnight. It was then allowed to cool to room temperature overnight. Small amounts of insoluble materials were filtered off using a glass-fiber filter paper. The filtrate was poured into 11 liters of acetone. It was stirred for 5 minutes and was allowed to settle. The clear acetone supernatant was decanted off. The resulting amber oil was added to a mixture of 25 liters of acetone and 2.5 liters of methanol, and was stirred for 10 minutes. The resulting solid was collected on an 11.5 inch (29.2 cm) diameter funnel using a VWR #413 filter paper. The resulting solid was first washed with a mixture containing 10:1 acetone: methanol (5 liters), then with acetone (5 liters), and finally with P950 ligroin (5 liters). The solid was then air-dried on the funnel. The solid clumps were crushed and the powder was dried in a vacuum oven at 50° C. for 2 days, giving rise to 547 g (yield: 87.8%) of the desired Compound I-1.

EXAMPLE 2

Preferred Concentrated Fixer Additive Composition

A preferred concentrated fixer additive composition was prepared by mixing Compound I-1 (0.28 mol/l) in water.

This concentrated additive composition was tested for stability using the following three tests that are more rigorous that the minimal standards described above:

a) room temperature solubility of Compound I-1 (66 g) in 250 ml of water (0.28 mol/l), b) low temperature solubility of Compound I-1 as determined by placing 100 ml samples of the additive composition in a glass jar and holding them individually at 0° F. (−18° C.), 20° F. (−7° C.), 30° F. (−1° C.), 40° F. (4° C.), 50° F. (10° C.) and 70° F. (21° C.) for 14 days, and then observing any physical changes (such as precipitation) 24 hours thereafter in each composition, and c) solubility of Compound I-1 (66 g) in a 18.9 liter volume of commercially available KODAK Fixer and Replenisher Process E-6 AR at room temperature, and no observable precipitation, for at least 3 days.

Compound I-1 passed all three tests.

EXAMPLES 3–9

Additional Fixer Additive Compositions

Other concentrated additive compositions were prepared by adding Compounds I-1 (0.22 mol/l), I-2 (0.22 mol/l), I-3 (0.14 mol/l,), I-4 (0.20 mol/l), I-5 (0.22 mol/l), I-6 (0.20 mol/l) or I-7 (0.22 mol/l) to water as described in Example 2. These compositions were subjected to three stability tests as described in Example 2, except that the amount of compound used in tests a) and c) was 47 g instead of 66 g. All of these compounds passed all three stability tests.

EXAMPLE 10
Concentrated Fixing Composition

A preferred concentrated fixing composition was prepared by mixing the concentrated fixer additive of Example 2 and other components to provide the following formulation:

| | |
|---|---|
| Ammonium thiosulfate fixing agent | 4.76 mol/l |
| Compound I-1 | 0.0037 mol/l |
| Sodium metabisulfite | 0.6 mol/l |
| Ethylenediaminetetraacetic acid | 0.02 mol/l |
| Sodium hydroxide | 0.25 mol/l |
| pH | 6.18 |

EXAMPLE 11
Working Strength Fixing Composition

A working strength fixing composition was prepared by diluting the concentrated fixing composition of Example 10, ten times with water. The working strength fixing compositions were used both in processor fixing baths as well as fixing replenishers to process several commercially available color reversal photographic films in the following manner.

Samples of FUJICHROME Color Reversal Films, AGFACHROME Color Reversal Films and EKTACHROME Color Reversal Films were imagewise exposed and processed using the following processing sequence and noted conditions and processing compositions (all compositions are commercially available except for the fixing compositions):

COMPARATIVE EXAMPLE

A concentrated fixer additive composition was prepared by mixing Compound I-8 shown below (0.075 mol/l) in water.

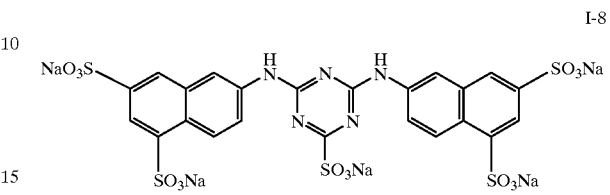

I-8

This compound was tested for stability using the three minimal standard stability tests a), b) and c) described above in the Summary of the Invention. Compound I-8 is outside the present invention and did not pass test c).

The invention has been described in detail with particular reference to certain preferred embodiments thereof, but it will be understood that variations and modifications can be effected within the spirit and scope of the invention.

| PROCESSING STEP | PROCESSING COMPOSITION | PROCESSING TIME | PROCESSING TEMPERATURE |
|---|---|---|---|
| First Development | KODAK First Developer, Process E-6 | 360 seconds | 38° C. |
| Washing | Water | 120 seconds | 38° C. |
| Reversal bath | KODAK Process E-6 AR Reversal Bath & Replenisher | 120 seconds | 38° C. |
| Color development | KODAK Color Developer, Process E-6 | 360 seconds | 38° C. |
| Conditioning or Prebleaching* | HUNT C6R Conditioner & Replenisher, or KODAK Prebleach Replenisher II, Process E-6, or KODAK Conditioner and Replenisher, Process E-6AR/MX-1600 | 120 seconds | 38° C. |
| Bleaching | KODAK Bleach, Process E-6 | 360 seconds | 38° C. |
| Fixing | Example 3 or 4 | 120 seconds, 240 seconds or 360 seconds | 38° C. |
| Washing | Water | 120 seconds | 38° C. |
| Stabilizing or Final rinsing* | HUNT C6R Stabilizer & Replenisher, Process E-6 or KODAK Final Rinse & Replenisher, Process E-6AR or KODAK Stabilizer and Replenisher, Process E-6AR/MX-1600 | 60 seconds | 38° C. |

*Some experiments were carried out using conditioning and stabilizing steps in the process, while other experiments were carried out using prebleaching and final rinsing steps in the process. The effects of the use of these different steps on the performance of the present invention were insignificant.

We claim:
1. A compound having Structure I
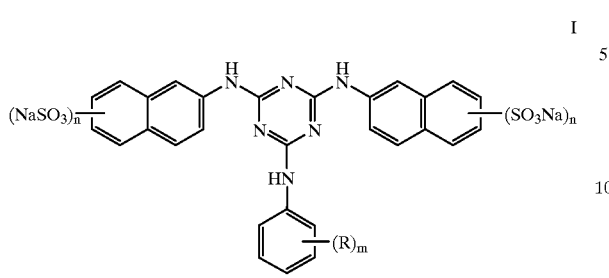
wherein R is carboxy or sulfo, m is an integer of from 0 to 5 and n is an integer of from 2 to 7.
2. The compound of claim 1 wherein R is carboxy, m is 1 or 2, and n is 2.
3. The compound of claim 1 wherein said compound of Structure I is:
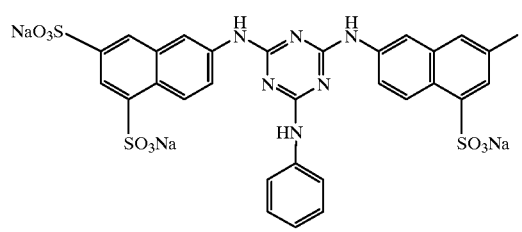
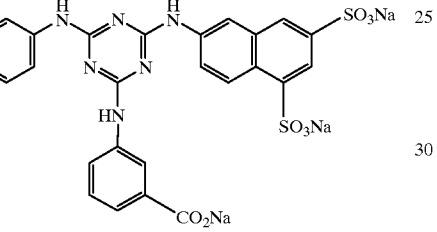
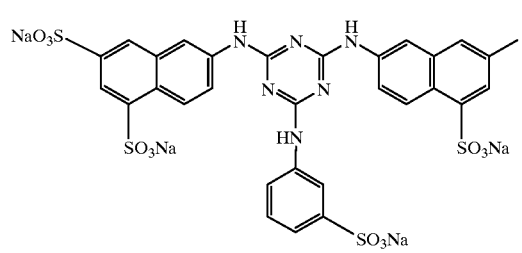
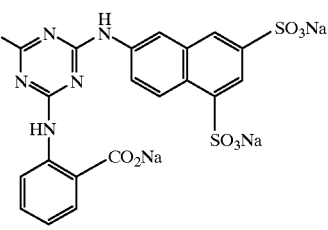
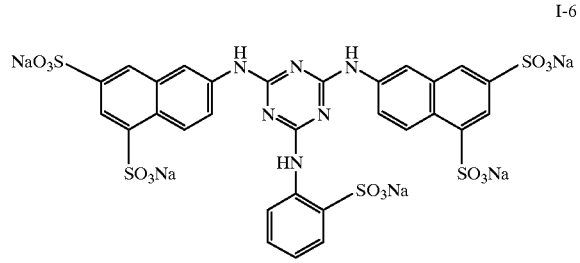
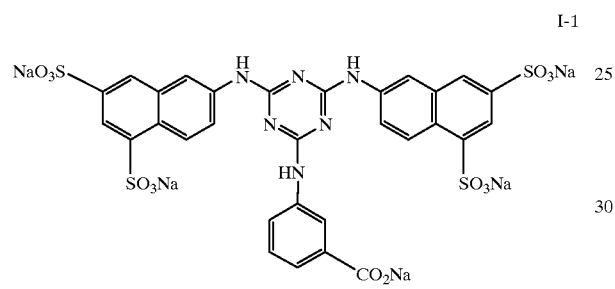
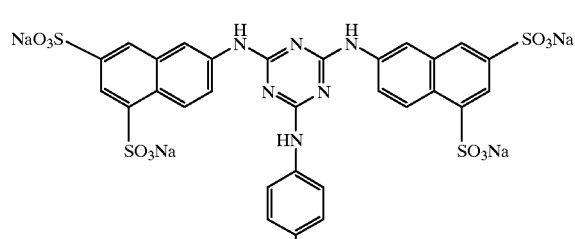
* * * * *